(12) United States Patent
Compans et al.

(10) Patent No.: US 6,838,080 B2
(45) Date of Patent: Jan. 4, 2005

(54) INDUCTION OF IMMUNOGLOBULIN CLASS SWITCHING BY INACTIVATED VIRAL VACCINE

(75) Inventors: Richard W. Compans, Atlanta, GA (US); Zhiyi Sha, Atlanta, GA (US)

(73) Assignee: Emory University, Atlanta, GA (US)

(*) Notice: Subject to any disclaimer, the term of this patent is extended or adjusted under 35 U.S.C. 154(b) by 0 days.

(21) Appl. No.: 09/733,166

(22) Filed: Dec. 8, 2000

(65) Prior Publication Data

US 2001/0031266 A1 Oct. 18, 2001

Related U.S. Application Data

(60) Provisional application No. 60/169,813, filed on Dec. 8, 1999.

(51) Int. Cl.$^7$ .................. A61K 39/145; A61K 39/21; C12N 7/04; C12N 7/06
(52) U.S. Cl. .................. 424/93.1; 24/208.1; 24/210; 24/211; 24/206.1; 24/93.3; 435/236; 435/238; 435/4; 435/5; 435/7.1; 435/7.2
(58) Field of Search .................. 424/93.1, 206.1, 424/208.1, 211.1, 93.3, 210.1; 435/236, 238, 4, 5, 7.2, 7.1

(56) References Cited

U.S. PATENT DOCUMENTS

| | | | |
|---|---|---|---|
| 4,790,987 A | 12/1988 | Compans et al. | 424/89 |
| 5,846,951 A | 12/1998 | Gregoriadis | 514/54 |
| 6,077,662 A | 6/2000 | Compans et al. | 435/5 |

OTHER PUBLICATIONS

Dorrell et al. International Journal of STD & AIDS 1997, vol. 8, pp. 776–779.*
MMWR 1997, vol. 46, No. RR–9, pp. 1–25.*
Smith et al. J. New Eng. Med. 1993, vol. 328, No. 6, pp. 373–379.*
ARUP's Guide to Clinical laboratory Testing, 2004.*
Brichacek et al. J. Infect. Dis. 1996, vol. 174, pp. 1191–1199.*
Levine et al. J. Acquired Immune Deficiency Syndromes and Human Retrovirology 1996, vol. 11, pp. 351–364.*
Jackson et al. Pediatric. Infect. Dis. J. 1997, vol. 16, No. 2, pp. 200–204.*
Dominic et al. Virol. 1996, vol. 224, pp. 10–17.*
Miotti et al. JAMA 1989, vol. 262, pp. 779–783.*
Pales et al. J. Inf. Dis. 1997, vol. 176 (Suppl 1), pp. S45–S49.*
Li et al. J. Virol. 1993, vol. 67, pp. 6659–6666.*
Muster et al. J. Virol. 1994, vol. 68, pp. 4031–4034.*
Chiba et al. Arch Virol, Aug. 1999, vol. 144, pp. 1469–1485.*
Murphy et al. Vaccine 1990, vol. 8, pp. 497–502.*

Bachmann et al. (Jul. 1993), "Formalin Inactivation of Vesicular Stomatitis Virus Impairs T–Cell– but Not T–Help–Independent B–Cell Responses," *J. Virol* 67(7):3917–3922.
Bachmann et al. (Dec. 1995), "T helper cell–indepenent neutralizing B cell response against vesicular stomatitis virus: role of antigen patterns in B cell induction?" *Eur. J. Immunol.* 25:3445–3451.
Davis et al. (Apr. 1993), "Evidence for a Stochastic Mechanism in the Differentiation of Mature Subsets of T Lymphocytes," *Cell* 73:237–247.
Finkelman et al. (1990), "Lymphokine Control of In Vivo Immunoglobulin Isotype Selection," *Annu. Rev. Immunol.* 8:303–333.
Freer et al. (Jun. 1994), "Vesicular Stomatitis Virus Indiana Glycoprotein as a T– Cell–Dependent and –Independent Antigen," *J. Virol.* 68:3650–3655.
Holaday et al. (Sep. 1991), "Reconstitution of *Leishmania* Immunity in Severe Combined Immunodeficient Mice Using Th1– and Th2–Like Cell Lines$^1$," *J. Immunol.* 147:1653–1658.
Horstmann, D.M. (May/Jun. 1979), "Maxwell Finland Lecture: Viral Vaccines and Their Ways," *Rev. Infect. Dis.* 1(3):502–516.
Horstmann, D.M. (Oct. 1982), "Control of Polimyelitis: A Continuing Paradox." *J. Infect. Dis.* 146:540–551.
Klenk et al. (1993), "The Characterization of Influenza A Viruses by Carbohydrate Analysis," *Curr. Top. Microbiol. Immunol.* 104:247–257.
Locksley et al. (Sep. 1993), "Helper T Cells Without CD4: control of Leishmaniasis in CD4–Deficient Mice," *Science*. 261:1448–1451.
Maloy et al. (Feb. 1998), "Interferon γ–producing γδT cell–dependent antibody isotype switching in the absence of germinal center formation during virus infection," *Proc. Natl. Acad. Sci. USA* 95:1160–1165.
Mitchell, G.F. (1983), "Murine Cutaneous Leishmaniasis Resistance in Reconstituted Nude Mice and Several $F_1$ Hybrids Infected with Leishmania Tropica Major," *J. Immunogenet.* 10:395–412.

(List continued on next page.)

*Primary Examiner*—James Housel
*Assistant Examiner*—Bao Qun Li
(74) *Attorney, Agent, or Firm*—Greenlee Winner and Sullivan PC

(57) ABSTRACT

The present disclosure provides methods and compositions for inducing an immune response to an antigen, especially in an immunogenic composition comprising sialic acid where the antigen comprises sialic acid and wherein the immunogenic composition further comprises a sialic acid binding component, e.g., an inactivated or attenuated paramyxovirus or orthomyxovirus such as an influenza virus comprising a sialic acid binding component, e.g., a neuraminidase. The compositions comprising sialic acid and a sialic acid binding component effectively induce a humoral immune response even in a human or animal which is deficient in CD4+ T cells, due to a disease such as ARC or AIDS, and there is also an immunoglobulin class switching even in the absence of CD4+ T cells.

2 Claims, 7 Drawing Sheets

OTHER PUBLICATIONS

Mombaerts et al. (Nov. 1992), "Mutations in T–cell antigen receptor genes α and β block thymocyte development at different stages ,"*Nature* 360:225–231.

Mombaerts et al. (Dec. 1992), "Mutations in T –cell antigen receptor genes α and β block thymocyte development at different stages ,"*Nature* 360(6403):491, (published erratum).

Mombaerts et al. (Apr. 1994), "Peripheral lymphoid development and function in TCR mutant mice,," *Int. Immunol.* 6(7):1061–1070.

Mond et al. (1995), "T Cell–Independent Antigens Type 2," *Annu. Rev. Immunol.* 13:655–692.

Mond et al. (1995), "T cell independent antigens," *Curr. Opin. Immunol.* 7:349–354.

Mosier et al. (Dec. 1977), "The Ontogeny of Thymic Independent Antibody Responses In Vitro in Normal Mice and Mice with an X–Linked B Cell Defect," *J. Immunol.* 119(6):1874–1878.

Oxenius et al. (1998), "CD4+ T–Cell Induction and Effector Functions: A Comparison of Immunity Against Soluble Antigens and Viral Infections," *Adv. Immunol.* 70:313–367.

Parker, D.C. (1993), "T Cell–Dependent B Cell Activation," *Annu. Rev. Immunol.* 11:331–360.

Pertmer et al. (Sep. 1996), "Influenza Virus Nucleoprotein–Specific Immunoglobulin G Subclass and Cytokine Responses Elicited by DNA Vaccination Are Dependent on the Route of Vector DNA Delivery,"*J. Virol.* 70(9):6119–6125.

Rahemtulla et al. (Sep. 1991), "Normal development and function of CD8 + cells but markedly decreased helper cell activity in mice lacking CD4," *Nature* 353:180–184.

Sha et al. (Feb. 1999), "Enhancement of Mucosal Immune Responses to the Influenza Virus HA Protein by Alternative Approaches to DNA Immunization," *Immunobiol.* 200:21–30.

Sha, Z. and Compans, R.W. (Jun. 2000), "Induction of CD4 + T–Cell– Independent Immunoglobulin Responses by Inactivated Influenza Virus," *J. Virol.* 74(11):4999–5005.

Snapper, C.M. and Mond, J.J. (Jan. 1993), "Towards a Comprehensive View of Immunoglobulin Class Switching," *Immunol. Today* 14:15–17.

Szomolanyi–Tsuda, E. and Welsh, R.M. (Feb. 1996), "T Cell–independent Antibody–mediated Clearance of Polyoma Virus in T Cell–deficient Mice," *J. Exp. Med.* 183:403–411.

Szomolanyi–Tsuda et al. (Aug. 1998), "T–Cell–Independent Immunoglobulin G Responses in Vivo Are Elicited by Live–Virus Infection but Not by Immunization with Viral Proteins or Virus–Like Particles," *J. Virol.* 72(8):6665–6670.

Szomolanyi–Tsuda, E. and Welsh, R.M. (Aug. 1998), "T–cell–independent antiviral antibody responses," *Curr. Opin. Immunol.* 10:431–435.

Viney et al. (Dec. 1994), "Lymphocyte proliferation in mice congenitally deficient in T–cell receptor αβ cells," *Proc. Natl. Acad. Sci.* USA 91:11948–11952.

Weis et al. (Jun. 1988), "Structure of the influenza virus haemagglutinin complexed with its receptor, sialic acid," *Nature* 333(2):426–431.

Wen et al. (May 1996), "Germinal Center Formation, Immunoglogulin Class Switching, and, and Autoantibody Production Driven by 'Non α/β' T Cells," *J. Exp. Med.* 183:2271–2282.

Berglund et al., (Feb. 1999) "Immunization with recombinant semliki Forest virus induces protection against influenza challenge in mice," *Vaccine* 17:497–507.

Budowsky et al., (1993), "Principles of selective inactivation of viral genome. VIII. The influence of β–propiolactone on immunogenic and protective activities of influenza virus," *Vaccine* 11(3):343–348.

McGill, P.E., (Feb. 1995), "Viral infections: alpha–viral arthropathy," Abstract #95246151.

Trépo et al., (1997), "The First *Flaviviridae* Symposium," *Intervirology* 40:279–288.

Valmori et al., (May 1999) "An Antigen–targeted Approach to Adoptive Transfer Therapy of Cancer[1]," *Cancer Research* 59:2167–2173.

* cited by examiner

INDUCTION OF IMMUNOGLOBULIN CLASS SWITCHING BY INACTIVATED VIRAL VACCINE

CROSS-REFERENCE TO RELATED APPLICATIONS

This application claims priority from U.S. Provisional Application No. 60/169,813 filed Dec. 8, 1999.

ACKNOWLEDGEMENT OF FEDERAL RESEARCH SUPPORT

This invention was made, at least in part, with funding from the National Institutes of Health (Grant No. AI-28147). Accordingly, the United States Government has certain rights in this invention.

BACKGROUND OF THE INVENTION

The field of the present invention is immunology, especially the area of vaccines, and in particular to compositions and methods for generating immune response to sialic acid-containing immunogenic compositions, which further contain a sialic acid binding component such as an orthomyxovirus or a paramyxovirus or an orthomyxovirus.

T cell-independent (TI) antigens are antigens that stimulate antibody responses in the absence of MHC class II-restricted T cell help. TI antigens fall into two major categories, TI type 1 (TI-1) and TI type 2 (TI-2). TI-1 antigens are characterized by being mitogenic and inducing polyclonal B cell proliferation. TI-2 antigens, which are represented by polysaccharides, have the properties of a high molecular weight, repeating antigenic epitopes, and inability to stimulate MHC class II-dependent T cell help (Mond et al. (1995a) *Annu. Rev. Immunol.* 13:655; Mond et al. (1995b) *Curr. Opin. Immunol.* 7:349; and Mosier et al. (1977) *J. Immunol.* 119:1874.) TI antigens induce only IgM responses. In contrast, protein antigens are thought to induce only T cell-dependent antibody responses, which include both IgM and IgG responses (Mond et al. (1995a) supra; Mond et al. (1995b) supra).

Two kinds of viral vaccines are currently being widely used: live attenuated viruses and formalin inactivated viruses. Live attenuated vaccines usually lead to excellent, often life-long, immunity to the vaccinated pathogen (Sabin et al. (1985) *J. Infect. Dis.* 151:420; and Salk, J., and Salk D. (1977) *Science* 195:834). However, in some instances, live attenuated viral vaccines can regain their virulence and cause serious complications (Evans et al. (1985) *Nature* 314:548; and Nkowane et al. (1987) *Jama* 257:1335). Inactivated vaccines are the only currently available vaccines for some diseases, including influenza. Disadvantages of the inactivated vaccines are that they induce lower titers of antibody, restricted isotype pattern, shorter duration of immunity and lack of cell-mediated immunity. (Horstmann, D. M. (1979) *Rev. Infect. Dis.* 1:502; and Horstmann, D. M. (1982) *J. Infect. Dis.* 146:540).

CD4 T helper cells are believed to be essential for induction of a high-affinity antibody response and for efficient isotype switching from IgM to IgG production (Oxenius et al. (1998) *Adv. Immunol.* 70:313; and Parker, D. C. (1993) *Annu. Rev. Immunol.* 11:331).

Through cognate interaction between antigen specific B cell and CD4 αβ T cells, the CD4+ αβ T cells secrete cytokines that initiate the immunoglobulin class switching process from IgM to IgG (Parker, D. C. (1993) *Annu. Rev. Immunol.* 11:331; Finkelman et al. (1990) *Annu. Rev. Immunol.* 8:303; and Snapper, C. M. and Mond, J. J. (1993) *Immunol. Today* 14:15). These T cell dependent antibody responses are accompanied by the formation of germinal centers of B cells in the lymphoid organs such as the spleen and lymph nodes. Recent studies have shown that Ig class switching can also be induced in T cell deficient mice when infected with live viruses (Maloy et al. (1998) *Proc. Natl. Acad. Sci. USA* 95:1160; Szomolanyi-Tsuda, E. and Welsh, R. M. (1996) *J. Exp. Med.* 183:403; and Szomolanyi-Tsuda et at. (1998) *J. Virol.* 72:6665). When T cell deficient mice (T cell receptor β chain knockout [TCRβ-/-] or T cell receptor α chain knockout [TCRα-/-] were infected with live polyoma viruses, a protective, virus-specific IgG response was reported in the absence of helper T cells. However, virus-like particles and soluble capsid antigens (VP1) were reported not to induce detectable IgG responses. In studies with VSV, TCRα-/- mice were found to produce neutralizing IgG antibodies when infected with live VSV or with a recombinant vaccinia virus expressing the VSV glycoprotein (Maloy et al. (1998) supra). These results suggest that there may be alternative mechanisms for antibody class switching and induction of IgG responses.

Formalin inactivation of VSV was reported to have no effect on the early IgM response after immunization, but class switching from IgM to IgG was significantly reduced (Freer et al. (1994) *J. Virol.* 68:3650; Bachmann et al. (1993) *J. Virol* 67:3917; and Bachmann et al. (1995) *Eur. J. Immunol.* 25:3445). Low doses ($2 \times 10^4$ PFU) of inactivated VSV virus did not induce any measurable neutralizing IgG responses, while high IgG titers were produced after immunization with the same dose of live viruses. Higher dose ($2 \times 10^6$ PFU and $1 \times 10^8$ PFU) of inactivated VSV viruses induced almost normal level of neutralizing IgG titers. However, when nude mice or mice depleted of CD4+ T cells by anti-CD4 monoclonal antibody were immunized with inactivated virus, no detectable virus-specific IgG was produced (Bachmann et al. (1993) *J. Virol.* 67:3917). It was therefore concluded that CD4+ T cells were strictly required for the generation of class switching from IgM to IgG when inactivated virus vaccines are used.

There is a need in the art for effective methods for immunization of immune compromised humans and animals, particularly those humans and animals who are deficient in CD4+ T cells, and for improved methods for immunization of humans and animals in general. The present invention fulfills this need.

SUMMARY OF THE INVENTION

The present invention provides for CD4+ T cell independent development of protective immune responses in response to sialic acid-containing vaccine compositions administered together with a sialic acid binding composition, as specifically exemplified by a formalin-inactivated influenza virus composition. Alternatively, non-infectious virus like particles of influenza virus or other virus (especially a paramyxovirus) exhibiting sialic acid binding activity can be complexed with a sialic acid containing target antigen for the development of a protective immune response, where that antigen is derived from a pathogen, including but not limited to those pathogens with sialic acid residues such as bacteria, viruses, protozoan, yeast and fungi. Desirably, the sialic acid is located at a location distal to a cell surface or a virus particle surface so that it is accessible for complex formation by the sialic acid binding material of the virus preparation. Desirably, the sialic acid binding preparation is an inactivated or attenuated virus, as specifically exemplified, the influenza virus preparation is a formalin-inactivated virus preparation. In principle, the sialic acid containing vaccine composition can be any antigen which contains accessible sialic acid. This development of protective immunity in a CD4− independent manner is applicable to AIDS and ARC in humans and in humans with CD4+ T cell deficiency of other origins and to similarly immune compromised animals, e.g., cats infected with feline immunodeficiency virus and cattle infected with bovine immunodeficiency virus. Examples of immunity include immunity to pathogenic *Escherichia coli* with a sialic acid capsule, *Neisseria meningitidis* with a polysialic acid capsule or tumor cells having glycosylation with terminal sialic acid residues, among others, and viruses comprising sialic acid residues, including without limitation, enveloped viruses (including HIV, SIV, FIV and others) and those viruses with glycoproteins having terminal sialic acid residues. Additional virus examples are vesicular stomatitis virus, rabies virus, measles virus, flavivirus, and alphaviruses and herpes viruses.

The present invention further provides for the development of desired classes of immunoglobulins in animals or humans deficient in CD4+ T cells, where the immunoglobulin is specific for an antigen which comprises sialic acid, with the sialic acid being present as part of the antigen such that it can be bound by a sialic acid binding moiety, as specifically exemplified by a formalin inactivated preparation of influenza virus. This is accomplished by the administration of the sialic acid containing antigen of interest together with a sialic acid binding composition, as embodied by a formalin-inactivated influenza virus preparation or an inactivated paramyxovirus preparation.

As an alternative, the influenza virus preparation (or other paramyxovirus preparation) can be treated with a protease, for example, chymotrypsin, to inactivate the neuraminidase. The absence of active neuraminidase in the immunogenic composition is believed to improve the stability of the advantageous combination of antigen sialic acid and sialic binding activity of the influenza virus or other paramyxovirus.

Without wishing to be bound by any particular theory, it is believed that the hemagglutinin component of the influenza virus (or paramyxovirus) binds to the sialic acid residue. In the alternative, and again, without wishing to be bound by theory, a viral component may mediate binding to an immune system cell to facilitate the development of a protective humoral immune response.

As an alternative to mixing a sialic acid containing antigen with a sialic acid binding paramyxovirus, e.g., influenza virus, preparation, one of ordinary skill in the art can prepare phenotypically mixed virus like particles, which particles comprise the sialic acid binding component (e.g., hemagglutinin) as well as the desired antigen. Such noninfectious particles can be used in immunogenic composition for the generation of a protective humoral immune response in a CD4-deficient human or animal. Phenotypically mixed viruses can also be prepared by coexpression of paramyxovirus coding sequences including the sialic acid binding component and the sialic acid containing antigens of another virus (e.g., those genes required for the production of virus like particles). For discussion of production of virus like particles of retroviruses, see U.S. Pat. No. 6,077,662 and references cited therein.

A further use of the immunogenic compositions of the present invention is in the generation of protective immunity, especially humoral immunity, in a shorter time than traditional immunogenic compositions, in CD normal animals or humans.

Optionally, the immunogenic compositions of the present invention can further comprise immunological adjuvants as well known to the art, and as discussed below. With or without the addition of immunological adjuvants, the immunogenic compositions of the present invention can be administered by intranasal, intragastric, oral, rectal, vaginal, lower respiratory, intramuscular, intradermal or subcutaneous routes. Booster administrations desirably follow the initial dosage.

BRIEF DESCRIPTION OF THE DRAWINGS

FIG. 5A: ♦: Control, unimmunized CD4+ T cell deficient C57B/mice. FIG. 5B: ●: CD4+ T cell deficient C57B/6 mice immunized with inactivated PR8 virus. FIG. 5C: ▲: CD8 T cell depleted CD4+ T cell deficient C57B/6 mice immunized with inactivated PR8 virus. One experiment of two with comparable results is shown.

DETAILED DESCRIPTION OF THE INVENTION

Abbreviations used in the present application include TI: T cell-independent, TD: T cell dependent, KO: knockout, TCR: T cell receptor, MHC: major histocompatibility complex, Ig: immunoglobulin, PR8: PR/8/34 influenza virus, VSV: vesicular stomatitis virus, mAb: monoclonal antibody, i.m.: intramuscularly, i.p.: intraperitoneally DN: double negative, $LD_{50}$: dose needed to kill half the experimental animals and FACS: fluorescence-activated cell sorting.

The present Specification describes an investigation of sialic acid binding components present in an immunogenic compositions, as specifically exemplified by formalin-inactivated influenza virus A/PR8, and the ability of those immunogenic compositions to induce an immune response including immunoglobulin class switching and virus-specific IgG production in the absence of CD4+ T cells.

Inactivated PR/8/34 influenza virus induces CD4+ T cell-independent IgG responses in mice. To investigate the potential of inactivated PR8 virus to induce IgG responses in the absence of CD4 T cells, the magnitude of virus-specific IgG responses to intramuscular immunization with inactivated PR8 viruses in normal C57B/6 mice and CD4 T cell deficient mice in a C57B/6 background were evaluated by measuring PR8 specific IgG concentrations by ELISA assay. 14–20 week old mice were used in this experiment. Formalin inactivated influenza virus strain PR8 was found to induce virus-specific IgM and IgG antibodies in normal C57B/6 mice. Analysis of the isotype distribution of the virus-specific IgG indicated that all four IgG subclasses were induced by the inactivated viruses, with IgG1 and IgG2a being predominant (FIG. 1). In the CD4+ T-cell deficient mice, an IgM response was induced in the absence of functional T helper cells in CD4 T-cell deficient mice. Furthermore, we also detected the presence of virus-specific IgG in the CD4 T-cell deficient mice, indicating that CD4+ T-cell independent antibody class switching from IgM to IgG took place after the immunization. All four IgG subclasses were induced, with IgG1 and IgG2A being the predominant virus-specific subclasses. The magnitude of the responses was, on the average, about 5-fold lower than that observed in the normal c57B/6 mice. Interestingly, IgA responses were not detected after the immunization in either CD4+ T-cell knockout mice or normal C57B/6 mice, indicating the lack of class switching to IgA after i.m. immunization with inactivated PR8 virus. These data indicate that IgG, but not IgA, responses can be induced by inactivated virus independent of CD4+ T helper cells.

Figure 1A:
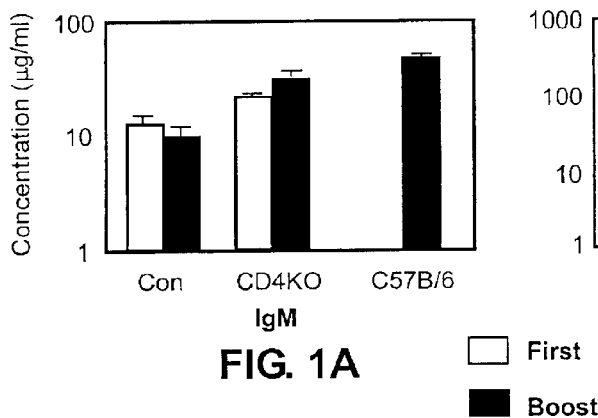
FIG 1: Magnitude and isotype profiles of serum antibody responses to intramuscular immunization with inactivated PR8 virus in CD4+ T cell deficient and immunocompetent mice. 16 week old CD4+ T cell deficient mice or C57B/6 mice were immunized intramuscularly with 10 μg/mouse of inactivated PR8 virus, mice were boosted with the same dose after 15 days. Con: Control, unimmunized CD4+ T cell deficient mice (n=5). CD4KO: CD4+ T cell deficient mice received inactivated PR8 virus (n=5). C57B/6: C57B/6 immunocompetent mice received inactivated PR8 virus (n=5). First: Samples were measured 15 days after first immunization. Boost: Samples were measured 10 days after boost. Serum samples were assayed in 1:400 and 1:1600 dilutions. One experiment representative of two with comparable results is shown.
Figure 1B:
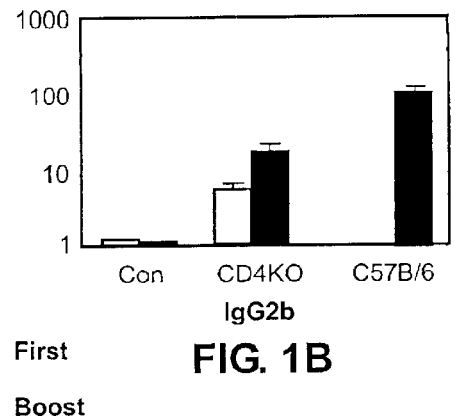
Figure 1C:
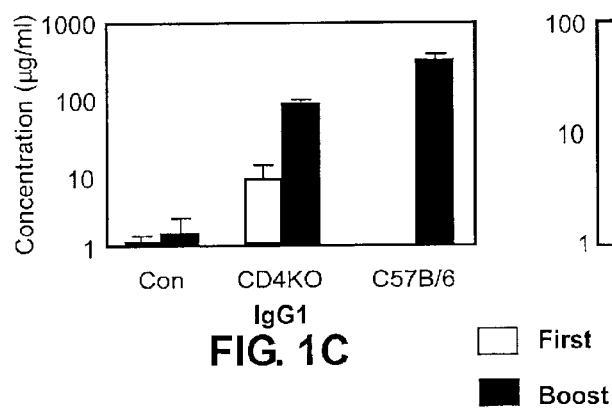
Figure 1D:
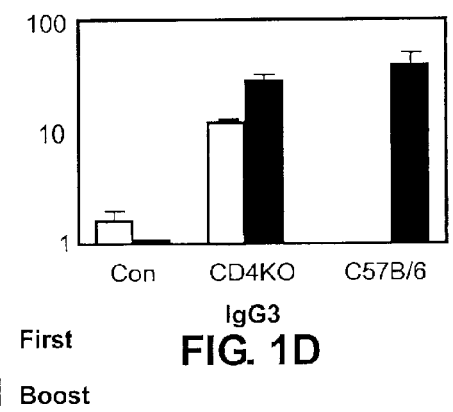
Figure 1E:
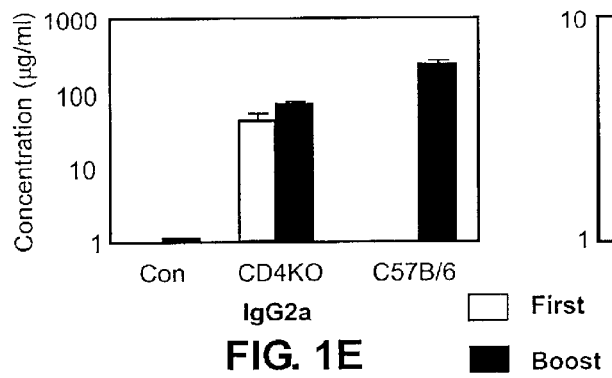
Figure 1F:
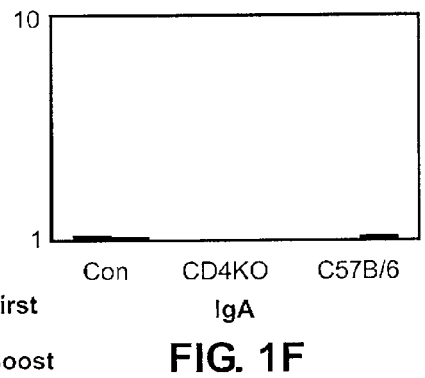
Figure 2:
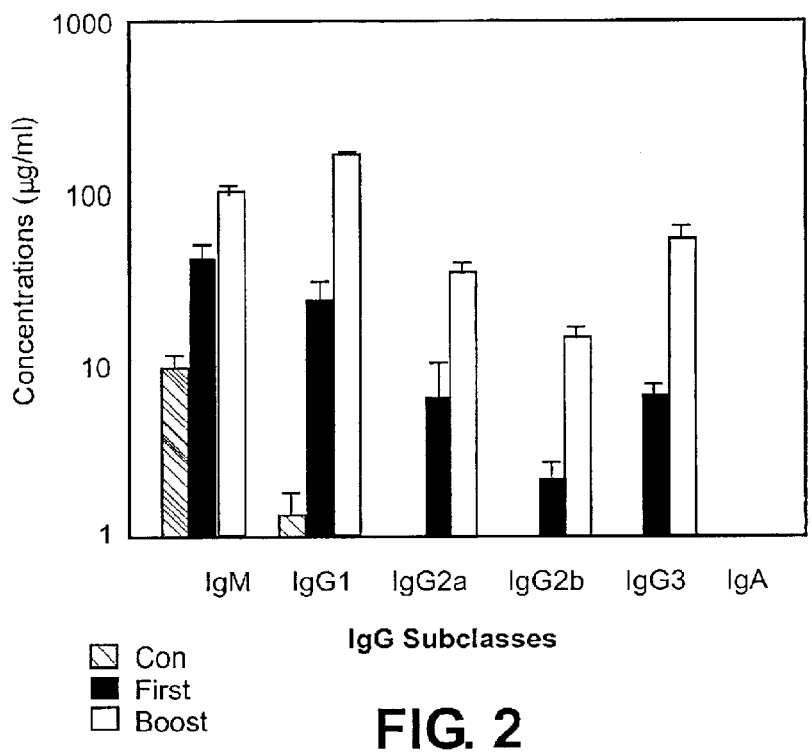
FIG. 2: Antibody responses and isotype distribution of virus-specific IgG in mice immunized intraperitoneally. CD4+ T cell deficient mice (n=5) were immunized intraperitoneally with formalin-inactivated PR8 influenza virus (10 μg/mouse) on day 0 and boosted on day 15. Serum samples were collected 15 days after priming and 10 days after boosting. Con: control, unimmunized CD4+ T cell deficient mice. First: after first immunization. Boost: after boost.

To examine whether or not the CD4+ T cell independent IgG responses in these experiments are specific to the intramuscular route, we immunized CD4+ T cell knockout C57B/6 mice intraperitoneally with formalin-inactivated PR8 virus. Analysis of the serum antibody indicated that both IgM and IgG were also induced by this route of immunization. All four subclasses of antibodies were detected, with IgG1 being the dominant response. The magnitude of these antibody responses is similar to those observed by the intramuscular route (FIG. 2). These data show that the CD4 T-cell independent Ig class switching elicited by inactivated virus can be induced by multiple routes, and that class switching is not specific to the i.m. route. Similar results are obtained with mucosal (nasal, oral, lower respiratory or intragastric) administration of the inactivated influenza virus.

Figure 3:
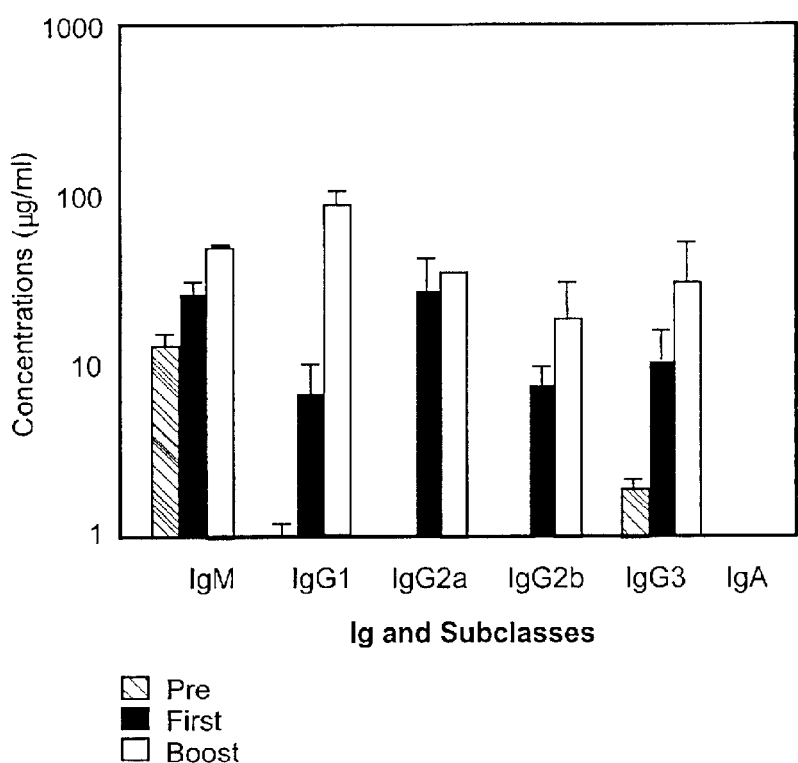
FIG. 3: Antibody responses and IgG isotype profile in CD8 depleted CD4+ T cell deficient C57B/6 mice after immunization with inactivated PR8 virus. CD4+ T cell deficient mice (n=5) were depleted of CD8 T cells by i.p. injection of 2.43 monoclonal antibody. These mice were then i.m. immunized with formalin-inactivated PR8 virus (10 μg/mouse) at day 0 boosted at day 15 with the same dose. Pre: serum samples before immunization. First: serum samples were taken at day 15 after first immunization. Boost: serum samples were taken at day 10 after boost.

CD8 T cells are not required for the induction of the CD4+ T cell independent IgG responses. It is generally believed that immunoglobulin isotype switching requires the interaction between B cells and CD4+ T cells, the latter secreting cytokines that regulate isotype switching. To investigate what types of cells are acting to "help" the induction of IgG responses in CD4+T cell deficient C57B/6 mice, we depleted the CD8+ T cells in these mice by injection of 2.43 monoclonal antibody (specific to CD4+ T cells). CD8+ T cells were found to be depleted by approximately 99% in peripheral blood when analyzed by FACS. Then CD4+ T cell deficient mice were immunized i.m. with inactivated PR8 virus, depletion of CD8+ T cells did not abrogate the IgG responses (FIG. 3). The magnitude and subclass profile of the IgG responses were found to be similar to those observed in the CD4+ T cell knockout mice without CD8+ T cell depletion. These results indicate that CD8+ T cells are not required for the inactivated virus-induced CD4+ T cell-independent IgG responses.

Figure 4:
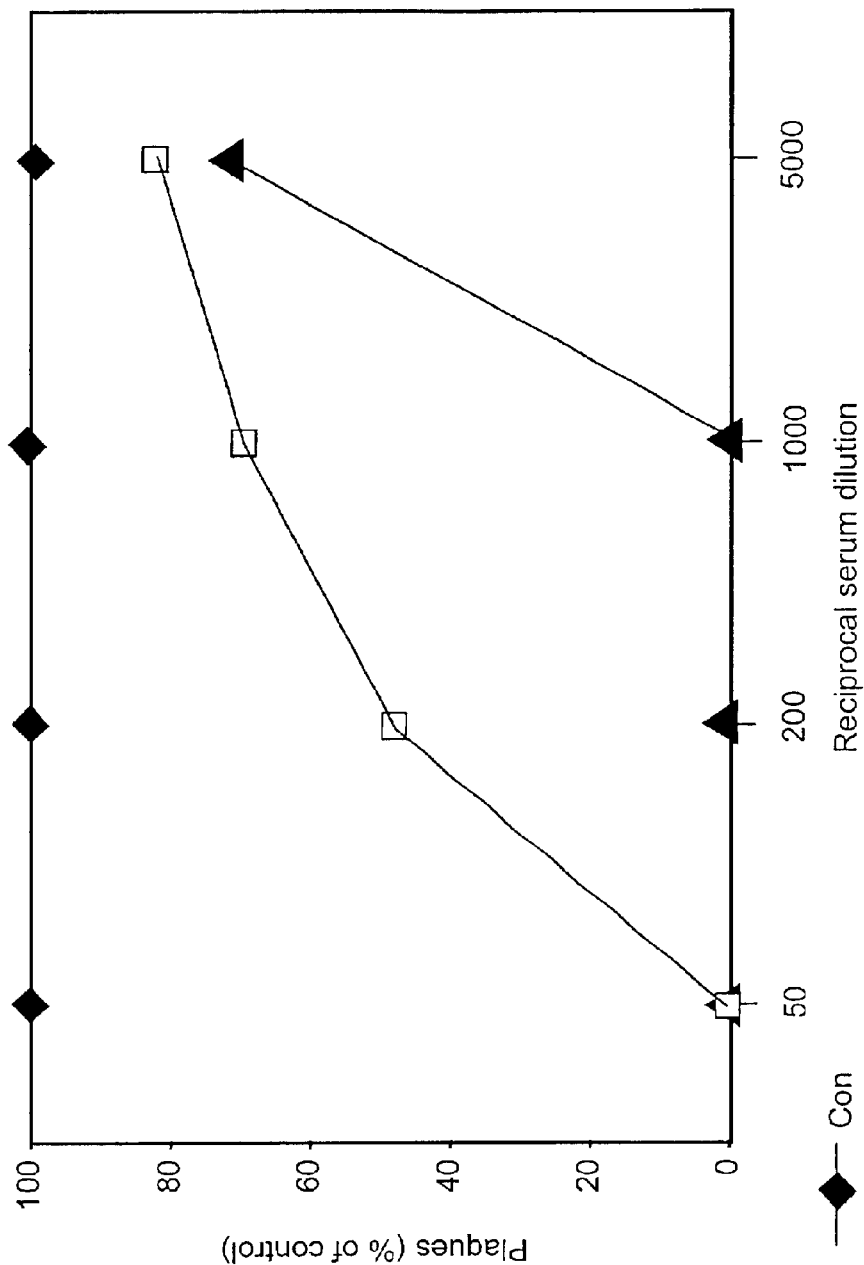
FIG. 4: Serum virus-neutralizing antibody titers in CD4+ T cell deficient C57B/6 mice i.m. immunized with formalin-inactivated PR8 virus CD4+ T cell deficient mice were i.m. immunized with formalin-inactivated PR8 virus (10 μg/mouse) at day 0 and boosted at day 15 with the same dose. Sera of different dilutions from immunized mice were mixed with 100 plaque forming unit of PR8 virus and incubated for 1 hr at room temperature. The mixtures were then used to infect a monolayer of MDCK cells, and a standard plaque reduction assay was performed. The neutralizing antibody titer of the serum is considered the highest dilution that was found to reduce the number of the plaques by 50% or more. ♦: Control, serum from unimmunized CD4+ T cell deficient mice. ■: Serum from CD4+ T cell deficient C57B/6 mice 15 days after priming. ▲: Serum from CD4+ T cell deficient C57B/6 mice 10 days after boosting.

The inactivated PR8 virus induced antibodies in CD4+ T-cell deficient mice have neutralizing activity. To explore whether the antibodies induced by formalin-inactivated PR8 virus in CD4+ T cell-deficient mice have virus-neutralizing activity in vitro, approximately 100 plaque-forming units of PR8 virus were incubated with sera at different dilutions and a standard plaque reduction assay was performed on MDCK cells. The neutralizing titer of the sera of the CD4+ T-cell deficient mice after the priming was 1:200, and the titer was 1:1000 after boosting. In contrast, the neutralizing titer of the control sera was under 1:50 (FIG. 4). This result shows that the antibodies induced in the absence of CD4+ T cell have virus neutralizing activity in vitro. There is, similarly, virus neutralizing effect of the antibodies in vivo.

Figure 5A:
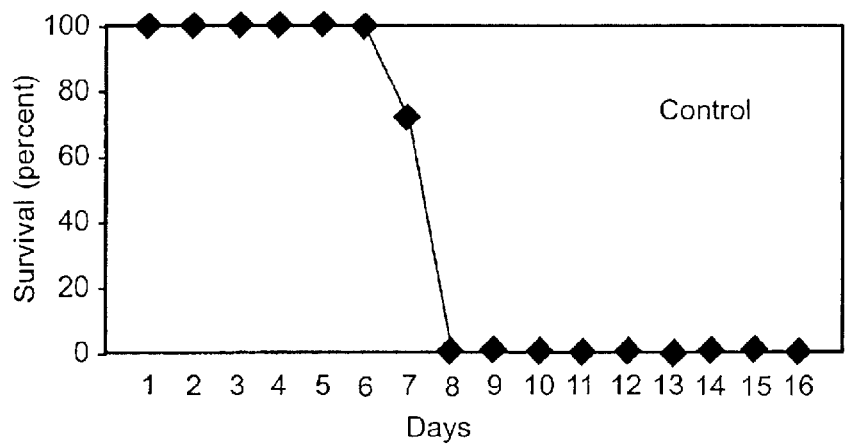
FIGS. 5A–5C: Protection of inactivated PR8 virus i.m. immunized CD4+ T cell deficient mice against live PR8 virus challenge. CD4+ T cell deficient C57B/6 mice i.m. immunized with inactivated PR8 virus were challenged intranasally with 10×LD50 doses of live PR8 virus under anesthesia 4 weeks after boost.
Figure 5B:
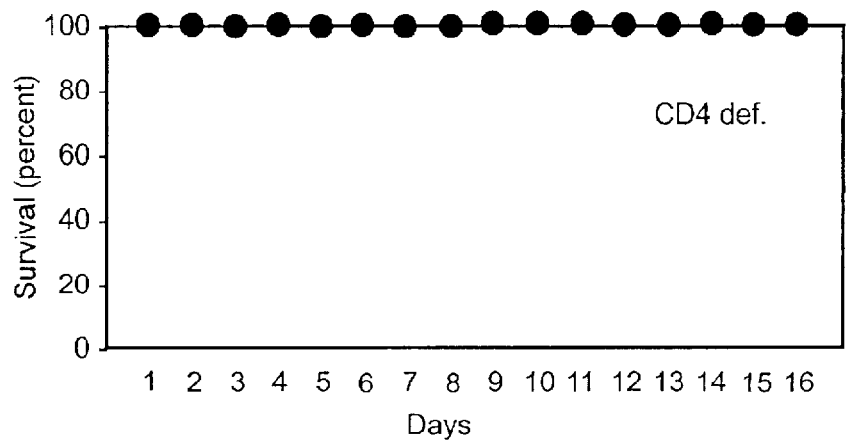
Figure 5C:
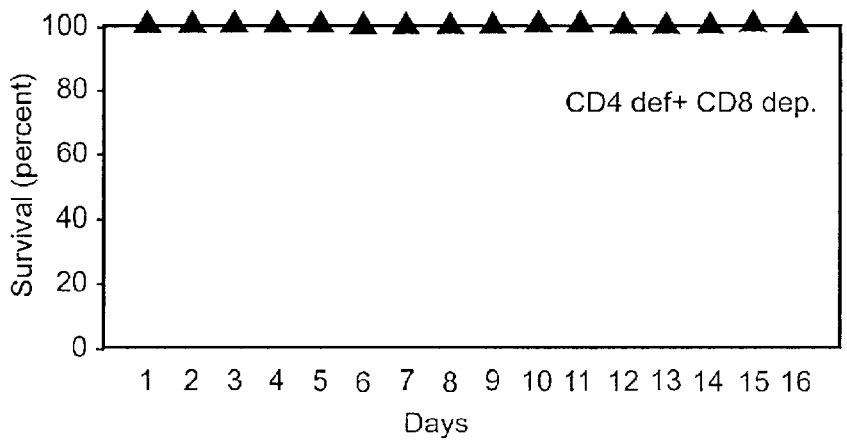
Figure 6A:
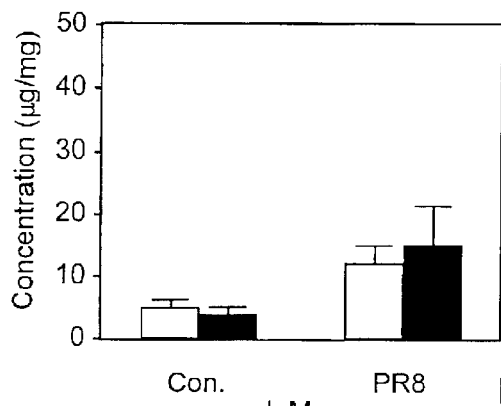
FIG. 6: Isotype profile of PR8 virus-specific antibody responses of T cell deficient mice. TCRβ−/− mice were i.m. immunized with formalin-inactivated PR8 viruses (10 μg/mouse) at day 0 and boosted at day 15. Serum samples were obtained 15 days after priming and 10 days after boosting. Con.: control, unimmunized TCRβ−/− mice; PR8: TCRβ−/− mice immunized with formalin-inactivated PR8 virus.
Figure 6B:
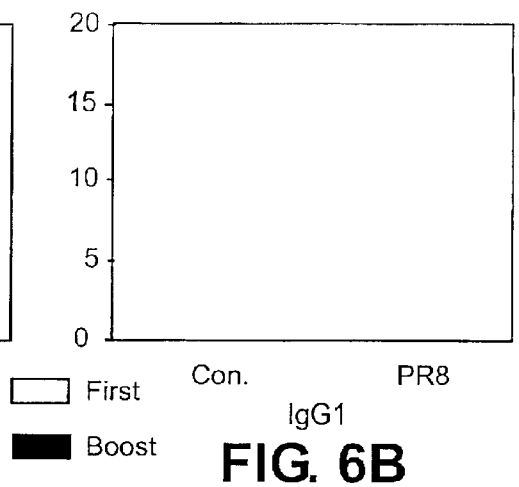
Figure 6C:
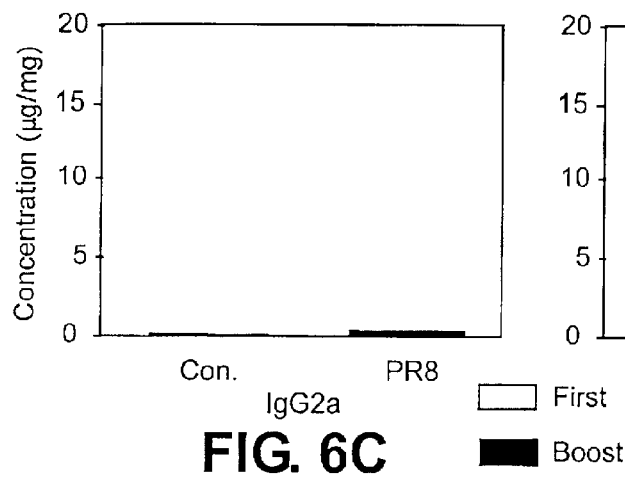
Figure 6D:
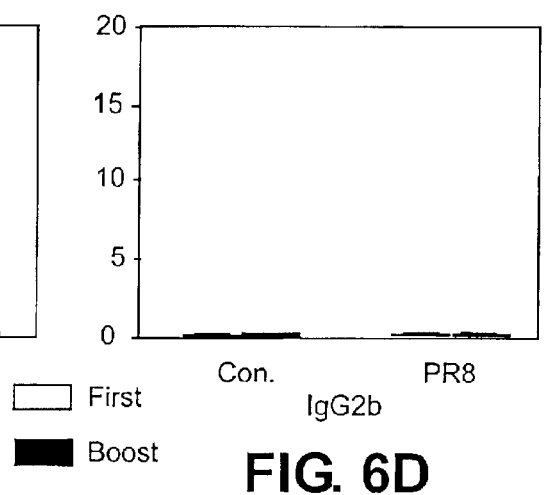
Figure 6E:
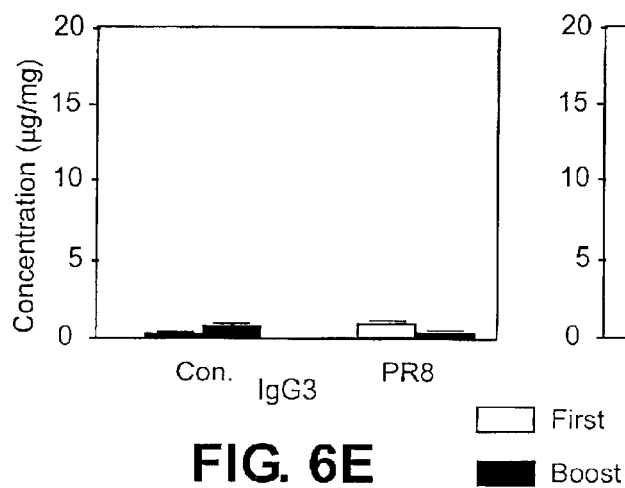
Figure 6F:
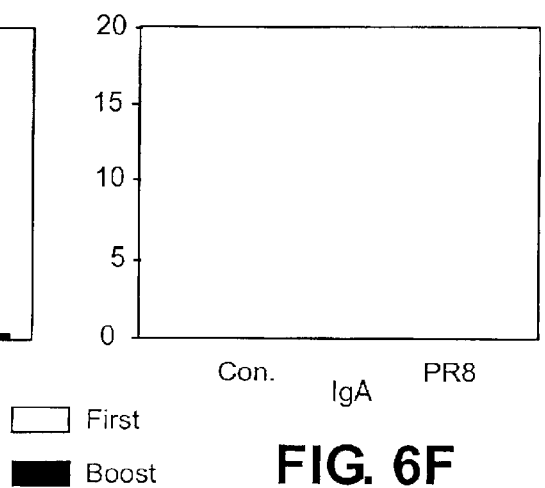

CD4+ T cell deficient mice are protected from live virus challenge after immunization with inactivated virus. To investigate whether the observed immune responses can protect against live virus challenge, the immunized CD4+ T-cell deficient mice were challenged with 10×LD50) intranasally under anesthesia. 100 percent of CD4+ T-cell deficient mice immunized with inactivated PR8 virus were protected from the live virus infection, and all the CD8+ T-cell depleted mice were also protected. In contrast, unimmunized CD4+ T-cell knockout mice all died on days 6–8 after the challenge (FIGS. 5A–5C). This indicates that inactivated virus induces fully protective immune responses without the participation of CD4+ T helper cells.

TcR $\alpha\beta^+$ T cell-deficient mice are unable to produce IgG responses after immunization with inactivated PR8 virus. To investigate whether mice deficient in total TcR $\alpha\beta+$ T cells were capable of mounting anti-viral IgG responses after immunization with inactivated influenza virus, we examined the virus-specific antibody responses of TcR$\beta$–/– mice after immunization with formalin-inactivated PR8 virus. We observed that TcR$\beta$–/– mice produced IgM responses after immunization with inactivated virus. The levels of IgM observed after the priming and boosting were similar. In contrast, however, the TcR$\beta$–/– nice did not develop significant virus-specific IgG responses after immunization with the inactivated PR8 virus. No IgG1, IgG2a or IgG2b responses could be detected, and only very low levels of IgG3 were produced (FIG. 6). These results indicate that although CD4+ and CD8+ T cells are not required, a certain population T cells is indispensable for IgG production after immunization with inactivated PR8 virus.

Figure 7:
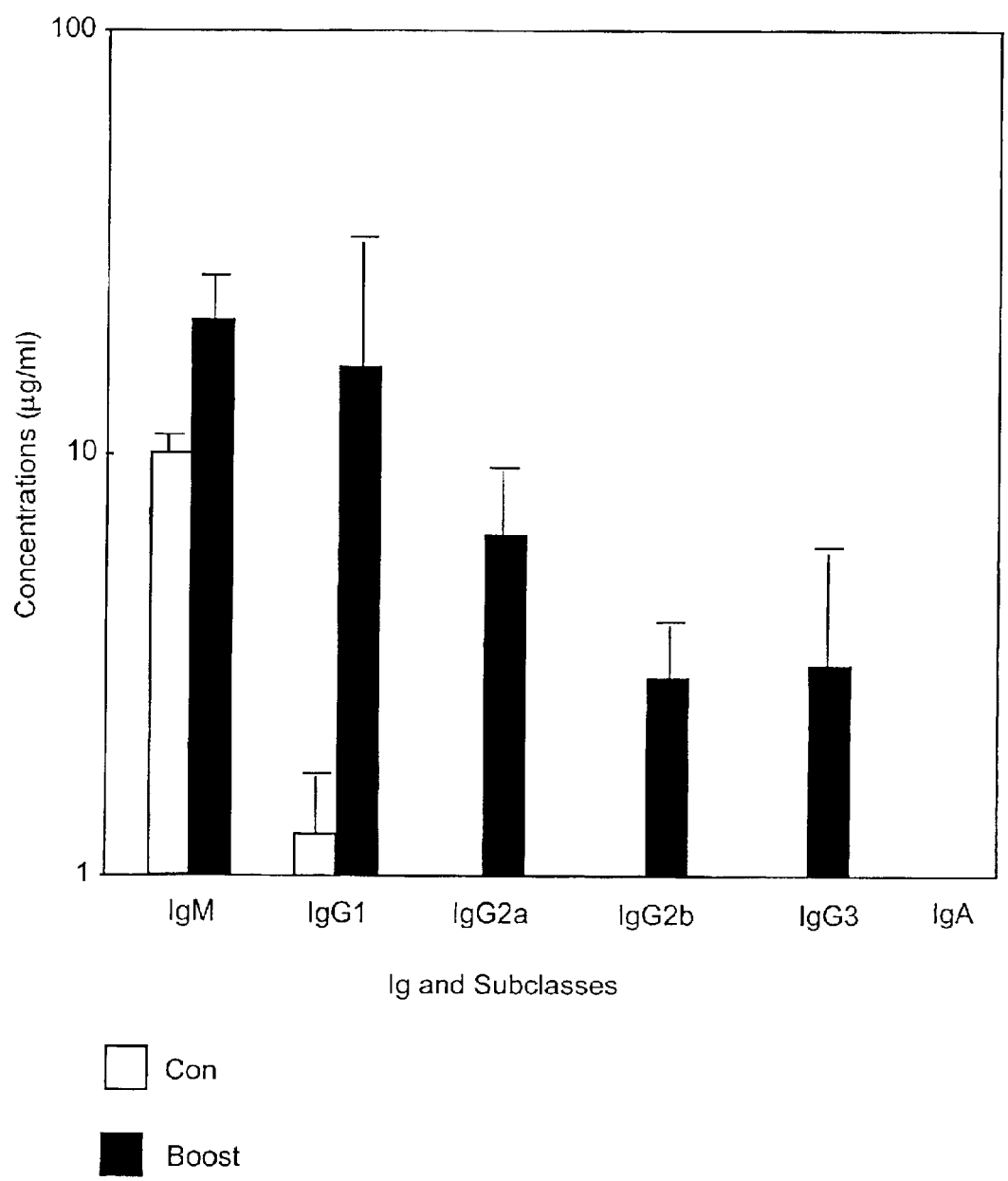
FIG. 7: Antibody responses and isotype distribution of virus-specific IgG in six week old mice i.m. immunized with inactivated PR8 virus. Six weeks old mice (n=4) were immunized intramuscularly with formalin-inactivated PR8 virus (10 μg/mouse) on day 0 and boosted on day 15. Serum samples were collected 10 days after boosting. Con: control, unimmunized CD4+ T cell deficient mice. Boost: serum samples after boost.

The magnitude of IgG responses to inactivated PR8 virus is age-dependent. We also examined whether younger CD4+ T cell knockout mice produced lower levels of IgG responses than older mice. In this experiment, 6 week old CD4+ T cell deficient C57B/6 mice were immunized intramuscularly with formalin-inactivated PR8 virus. A significant amount of IgM and all four subclasses of IgG were produced, but their levels on the average were 5–6 fold lower than those of the 16 week old mice. IgG1 is predominant among the four subclasses of IgG, similar to the pattern of that of the old mice (FIG. 7). These date indicate that younger CD4+ T cell knockout mice produce lower levels of IgG responses than older mice.

Figure 8A:
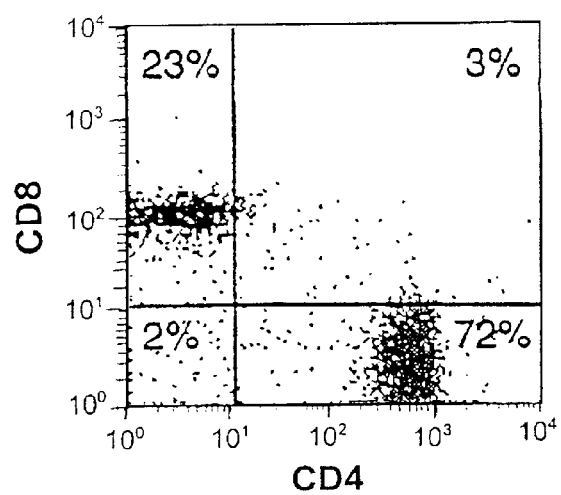
FIG. 8: Flow cytometry analysis of αβ T cells in CD4+ T cell deficient mice. Spleen cells from C57BL/6 mice or CD4+ T cell deficient mice were stained with anti-TCRβ, anti-CD8 and anti-CD4 monoclonal antibodies (H57-FITC, 53-6.7-PerCP and GK1.5-PE, respectively from PharMingen, Beckton-Dickinson). Plots show TCRβ-gated cells. (a) 16 week old C57BL/6 mouse. (b) 6 month old CD4+ T cell deficient mouse. (c) 6 week old CD4+ T cell deficient mouse.
Figure 8B:
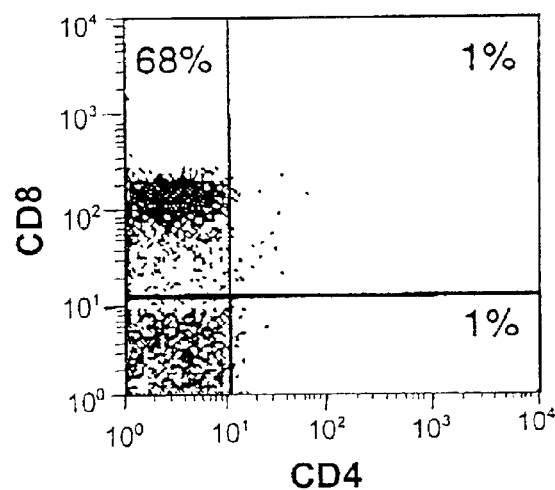
Figure 8C:
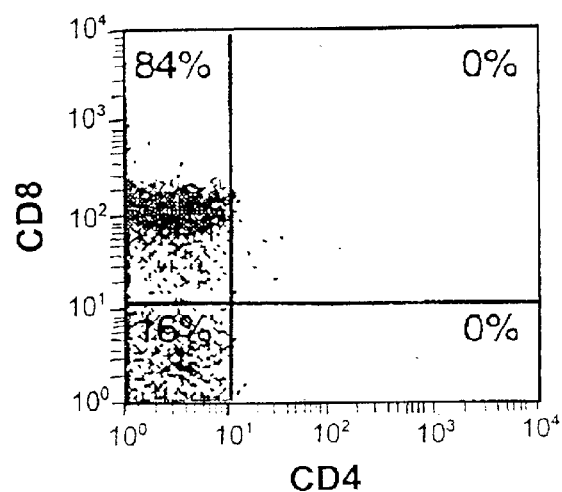

CD4+ T cell deficient mice produce more DN T cells in the spleen than normal C57BL/6 mice. To investigate whether CD4+ T cell deficient mice have the same DN T cell population as that of the normal C57B/6 mice, we analyzed different T cell populations in these mice by flow cytometry after staining the T cells with anti-TCR$\beta$, anti-CD8 and anti-CD4 monoclonal antibodies. In normal C57BL/6 mice, DN T cells account for about 2% of the T cell population. In contrast, DN T cells were found to constitute about 30% of the total T cell population in 6 month old CD4+ T cell deficient mice and about 15% in younger (6 week old) CD4+ T cell deficient mice (FIG. 8). These results demonstrate that higher level of DN T cells are produced in CD4 T cell deficient mice than in normal mice.

We show in this study that formalin-inactivated influenza PR8 virus induces IgM and IgG responses in the absence of CD4 T cells. All four subclasses of IgG were produced, with IgG1 and IgG2a being predominant. These antibodies have neutralizing activity against influenza virus in vitro and in vivo. The immunized CD4+ T cell deficient mice were shown to be protected from intranasal challenges with lethal doses of live PR8 viruses. To our knowledge, this is the first report that an inactivated virus can induce B cell differentiation and isotype switching from IgM to IgG that is completely independent of CD4+ T helper cells.

The ability of CD4+ T-cell deficient mice to generate IgG responses after immunization with inactivated PR8 virus was also not found to be impaired when these mice were depleted of CD8+ T cells by anti-CD8 mAb. In contrast, T cell deficient mice (TCR$\alpha$–/– and TCR$\beta$–/–) were not observed to produce significant amounts of IgG upon immunization with formalin-inactivated PR8 virus. These results suggest that CD4$^-$ and CD8$^-$ double negative T cells are playing a role in regulating immunoglobulin class switching in the absence of CD4+ T cells. To our knowledge, this is also the first evidence that CD4$^-$ and CD8$^-$ double negative $\alpha\beta$ T cells provide "help" to Ig class switching and generation of IgG antibody in the immune response against virus pathogens. Similarly, sialic acid containing bacterial and other antigens are also effective in generating an immune response when administered in the presence of a sialic acid binding agent in a CD4+ T cell deficient human or animal. The pathogenic target cell (bacterial, fungal, yeast, virus, enveloped virus, etc) is formulated into an immunogenic composition as described hereinbelow and as known to the art with approximately equal amounts of target cell material and sialic acid binding material (e.g., inactivated influenza or paramyxovirus material).

The presence of $CD4^-$ and $CD8^-$ double negative T helper cells in the $CD4^+$ T cell deficient mice is consistent with recent results from $CD4^+$ deficient mice infected with *Leishmania major* (Davis et al. (1993) *Cell* 73:237; and Locksley et al. (1993) *Science* 261:1448). T cell deficient nude mice and severe combined immunodeficient (SCID) mice cannot control *Leishmania major* infection and the fatal dissemination of the parasite (Holaday et al. (1991) *J. Immunol.* 147:1653; and Mitchell G. F. (1983) *J. Immunogenet.* 10:395). In contrast, the CD4−/− mice were reported to be resistant to the infection and resolution of the infection occurs within 6 weeks. The double negative TCR$\alpha\beta$+ T cells purified from infected CD4−/− mice were found to have IFN-$\gamma$ transcripts comparable in amounts to those in the $CD4^+$ population purified from infected CD4+/− animals (Locksley supra). The IFN-$\gamma$ production was also found to be comparable in these purified populations. Monoclonal antibody to IFN-$\gamma$ abrogated the ability of CD4−/− mice to recover from *Leishmania major* infection. Although $CD4^-$ and $CD8^-$ double negative $\alpha\beta$ T cells are present in normal mice, they account for only 2% of the T cells in the spleen. It is unlikely that this normal population plays a major role in Ig class switching in the presence of $CD4^+$ T cells. In contrast, we show in our study that DN T cells constitute of almost 30% of the T cell population in 6 months old $CD4^+$ T cell deficient mice. Without wishing to be bound by any particular theory, we believe that these DN T cells compensate for the functions of $CD4^+$ T cells which are absent in those mice. The quantitative difference of DN T cells between older and younger mice are believed to account for the different magnitude of antibodies produced in these $CD4^+$ T cell deficient mice. The younger mice (6 weeks old) were observed to have about 15% of DN T cells in their T cell population, while in older mice (6 months) 30% of the T cells were found to be DN T cells.

In studies with VSV, formalin inactivated virus was not observed to induce Ig class switching and IgG production in normal mice depleted of $CD4^+$ T cells, which differs from the results obtained with the influenza virus in our study. There are several possible explanations for these differences. First, there may be unique properties of influenza virus as an antigen. In contrast to VSV, influenza virions lack sialic acid on their surface (Klenk et al. (1983) *Curr. Top. Microbiol Immunol.* 104:247). In addition, influenza virions can bind efficiently to any cell surfaces that contain sialic acid because of the receptor binding activity of the HA glycoprotein (Weis et al. (1988) *Nature* 333:426), and their binding promotes cell-to-cell contacts that are involved in antibody induction. Second, there may also be differences between the effects of acute depletion of CD4$^+$ T cells in normal mice versus the development of the immune system in congenital CD4$^+$ T cell deficient mice in which a compensatory mechanism may develop, which is supported by the result that a large number of DN T cells exist in the spleen of the CD4$^+$ T cell deficient mouse shown in our study. This possibility is suggested by studies in mice with TNP-*Brucella abortis*, a T cell-independent antigen, to which nude mice produced higher TNP-specific IgG responses than normal mice depleted of CD4$^+$ T cells by mAb (Mond (1995a) supra; Maloy supra; Mombaerts et al. (1994) *Int. Immunol.* 6:1061; and Viney et al. (1994) *Proc. Natl. Acad. Sci. USA* 91:11948).

The current available data from some studies suggest that different antigens use different mechanisms and cells to induce Ig class switching in mice when the conventional TCRαβ$^+$ T cells are absent. In the case of VSV, the neutralizing IgG responses were crucially dependent on IFN-γ and were predominantly of the IgG2a subtype. This class switching effect was reported to be abolished when γδ T cells are absent, indicating the γδ T cells are providing the "help" for Ig class switching when αβ T cells are absent (Maloy supra). Studies with a mouse model of human systemic lupus erythematosus (SLE) had revealed that the reproducible production of IgG1 (including autoantibodies) is a product of non-αβ T cell help that can be provided by γδ$^+$ T cells (Wen et al. (1996) *J. Exp. Med.* 183:2271). This type of B-T interaction sustains the production of germinal centers that are usually the result of αβ T cell and B cell collaboration. In contrast, polyoma virus was reported to induce IgG responses both in TCRβ-/- mice and TCRβxδ-/- mice, with similar magnitude of the virus-specific IgG titer, suggesting that TCRγδ$^+$ T cells do not seem to play a role in helping the Ig class switching process for this virus antigen (Szomolanyi-Tsuda, E. and Welsh, R. M. supra; Szomolanyi-Tsuda supra; and Szomolanyi-Tsuda, E. and Welsh, R. M. (1998) *Curr. Opin. Immunol.* 10:431).

Our results indicate that the CD4$^-$ and CD8$^-$ double negative T cells trigger B cell proliferation, differentiation and isotype switching from IgM to IgG even in the complete absence of CD4$^+$ T helper cells. These findings have important practical implications. Usually, live attenuated vaccines are not administered to immunocompromised patients because of their potential to cause life-threatening infections. Inactivated virus vaccines would be the choice for use in these situations. In these patients, especially AIDS patients whose CD4 counts are extremely low, the "help" from CD4$^-$ and CD8$^-$ double negative T cells allows the generation of long-lasting protective IgG immune responses against viral pathogens by vaccination with inactivated viral vaccines even with an impaired CD4$^+$ T helper cell function. Similarly, other desired antigens can be administered together with an inactivated influenza virus or paramyxovirus preparation.

As used herein, an inactivated target tumor or pathogenic microbial cell or target virus is one which cannot cause a tumor or disease in a human or animal to which it is administered. Cells or viruses can be inactivated using heat treatment or formalin or β-propiolactone treatment, as known to the art.

An attenuated target cell (tumor cell or microbial pathogenic microorganism) does not cause a tumor or disease in a human or animal to which it is administered. Target cells can be attenuated, for example, by serial passage in the laboratory.

Flaviviruses include, without limitation, Dengue virus, yellow fever virus, St. Louis encephalitis virus, Japanese encephalitis virus, Murray Valley encephalitis virus, West Nile virus, Rocio virus, tick-borne encephalitis virus, Omsk hemorrhagic fever virus, Kyasanur Forest disease virus, or Powassan virus.

Alphaviruses include, but are not limited to, Sindbis virus, Semliki forest virus, Venezuelan equine encephalitis virus, eastern equine encephalitis virus, western equine encephalitis virus, Ross River virus, Mayaro virus, O'nyong-nyong virus or chikungunya virus.

The immunogenic compositions and/or vaccines are formulated by any of the means known in the art. They can be typically prepared as injectables or as formulations for intranasal administration, either as liquid solutions or suspensions. Solid forms suitable for solution in, or suspension in, liquid prior to injection or other administration may also be prepared. The preparation may also, for example, be emulsified, or the protein(s)/peptide(s) encapsulated in liposomes.

Where mucosal immunity is desired, the immunogenic compositions advantageously contain an adjuvant such as the nontoxic cholera toxin B subunit (see, e.g., U.S. Pat. No. 5,462,734). Cholera toxin B subunit is commercially available, for example, from the Sigma Chemical Company, St. Louis, Mo. Other suitable adjuvants are available and may be substituted therefor. It is preferred that an adjuvant for an aerosol immunogenic (or vaccine) formulation is able to bind to epithelial cells and stimulate mucosal immunity.

Among the adjuvants suitable for mucosal administration and for stimulating mucosal immunity are organometallopolymers including linear, branched or cross-linked silicones which are bonded at the ends or along the length of the polymers to the particle or its core. Such polysiloxanes can vary in molecular weight from about 400 up to about 1,000,000 daltons; the preferred length range is from about 700 to about 60,000 daltons. Suitable functionalized silicones include (trialkoxysilyl) alkyl-terminated polydialkylsiloxanes and trialkoxysilyl-terminated polydialkylsiloxanes, for example, 3-(triethyoxysilyl) propyl-terminated polydimethylsiloxane. See U.S. Pat. No. 5,571,531, incorporated by reference herein. Phosphazene polyelectrolytes can also be incorporated into immunogenic compositions for transmucosal administration (intranasal, vaginal, rectal, respiratory system by aerosol administration) (See e.g., U.S. Pat. No. 5,562,909).

The active immunogenic ingredients are often mixed with excipients or carriers which are pharmaceutically acceptable and compatible with the active ingredient. Suitable excipients include, but are not limited to, water, saline, dextrose, glycerol, ethanol, or the like and combinations thereof. The concentration of the immunogenic polypeptide in injectable, aerosol or nasal formulations is usually in the range of 0.2 to 5 mg/ml. Similar dosages can be administered to other mucosal surfaces.

In addition, if desired, the vaccines may contain minor amounts of auxiliary substances such as wetting or emulsifying agents, pH buffering agents, and/or adjuvants which enhance the effectiveness of the vaccine. Examples of adjuvants which may be effective include but are not limited to: aluminum hydroxide; N-acetyl-muramyl-L-threonyl-D-isoglutamine (thr-MDP); Nacetyl-nor-muramyl-L-alanyl-D-isoglutamine (CGP 11637, referred to as nor-MDP);

N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria: monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies (especially IgG, IgM or IgA) directed against the immunogen resulting from administration of the immunogen in vaccines which comprise the adjuvant in question. Such additional formulations and modes of administration as are known in the art may also be used.

An sialic acid containing antigen of interest or a peptide derived in sequence from a protein antigen of interest is formulated into vaccines as neutral or salt forms. Pharmaceutically acceptable salts include, but are not limited to, the acid addition salts (formed with free amino groups of the peptide) which are formed with inorganic acids, e.g., hydrochloric acid or phosphoric acids; and organic acids, e.g., acetic, oxalic, tartaric, or maleic acid. Salts formed with the free carboxyl groups may also be derived from inorganic bases, e.g., sodium, potassium, ammonium, calcium, or ferric hydroxides, and organic bases, e.g., isopropylamine, trimethylamine, 2-ethylamino-ethanol, histidine, and procaine.

The immunogenic compositions or vaccines are administered in a manner compatible with the dosage formulation, and in such amount and manner as will be prophylactically and/or therapeutically effective, according to what is known to the art The quantity to be administered, which is generally in the range of about 100 to 1,000 µg of protein per dose, more generally in the range of about 20 to 1000 µg of protein per dose, depends on the subject to be treated, the capacity of the individual's (or animal's) immune system to synthesize antibodies, and the degree of protection desired. Precise amounts of the active ingredient required to be administered may depend on the judgment of the physician or veterinarian and may be peculiar to each individual, but such a determination is within the skill of such a practitioner.

The vaccine or other immunogenic composition may be given in a single dose; two dose schedule, for example two to eight weeks apart; or a multiple dose schedule or in combination with other vaccines. A multiple dose schedule is one in which a primary course of vaccination may include 1 to 10 or more separate doses, followed by other doses administered at subsequent time intervals as required to maintain and/or reinforce the immune response, e.g., at 1 to 4 months for a second dose, and if needed, a subsequent dose(s) after several months. Humans (or other animals) immunized with the antigen administered according to the present invention are protected from infection by the pathogen from which the antigen of interest is derived.

The term antibody is used to refer both to a homogenous molecular entity, or a mixture such as a serum product made up of a plurality of different molecular entities. Monoclonal or polyclonal antibodies, preferably monoclonal, which specifically react with a particular protein or class of immunoglobulin, are made by methods well known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1999) vide infra. Also, recombinant immunoglobulins may be produced by methods known in the art, including but not limited to, the methods described in U.S. Pat. No. 4,816,567. Monoclonal antibodies with affinities of $10^8$ M$^{-1}$, preferably $10^9$ to $10^{10}$ or more, are preferred. Single chain antibodies are also known to the art.

Except as noted hereafter, standard techniques for peptide synthesis, cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part I; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold spring Harbor Laboratory, Cold Spring Harbor, N.Y., Old Primrose (1981) *Principles of Gene Manipulation*, University of California Press, Berkeley; Schleif and Wensink (1982) *Practical Methods in Molecular Biology*; Glover (ed.) (1985) *DNA Cloning* Vol. I and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York; Ausubel et al. (1999) *Current Protocols in Molecular Biology*, Wiley Interscience, New York, N.Y. Abbreviations and nomenclature, where employed, are deemed standard in the field and commonly used in professional journals such as those cited herein.

All references and patents cited in the present application are hereby incorporated by reference in their entirety to the extent that there is no inconsistency with the present disclosure.

The foregoing discussion and the following examples illustrate but are not intended to limit the invention. The skilled artisan will understand that alternative methods may be used to implement the invention, and variations in the exemplified compositions and methods are intended to fall within the scope of the present invention.

EXAMPLES

Example 1

Animals

C57BL/6J mice, C57BL/6-Cd4$^{tm/Mak}$, which had a targeted disruption in their CD4 gene and therefore lacked functional CD4$^+$ T cells (Rahemtulla, et al. (1991) *Nature* 353:180), C57BL/6J-Tcra$^{tm/Mom}$, which had a targeted disruption in their TCRα gene and lacked functional αβ T cells (Mombaerts et al. (1992) published erratum appears in *Nature* Dec. 3, 1992 360(6403):492. *Nature* 360:225) were obtained from the Jackson Laboratories (Bar Harbor, Me.). Some of the mice were bred in the Department of Animal Resources in Emory University from the breeding pairs purchased. Two age groups of mice were used in this study; one age group was 16–20 weeks old, the other age group was 6 weeks old.

Example 2

Viruses and Immunization and Sampling

Influenza virus strain A/PR/8/34 was grown in the allantoic cavity of 9–11 day old embryonated hen's eggs, and virus was purified from allantoic fluid by sucrose gradient centrifugation at 100,000×g. For inactivation, purified virus was mixed with formalin at a final concentration at 1:4000 (v/v) and incubated at 37° C. for 72 hours and then dialyzed against PBS with 3 changes. The virus stock was stored in aliquots at −80° C. before use. Inactivation of the virus was confirmed by both plaque assay on confluent monolayer MDCK cells and inoculation of the virus into 9–11 days old embryonated hen's eggs. For immunization, mice were immunized with 10 µg/ 100 µl of virus protein intramuscularly (i.m.) or intraperitoneally (i.p.) at day 0 and day 15. Blood samples were collected 15 days after priming and 10 days after boosting.

Anesthetized mice were bled from retroorbital veins to obtain blood samples. Samples were centrifuged at 14,000 rpm, and sera were stored at −20° C.

Example 3

In vitro Virus Neutralization Assay

A standard plaque reduction assay was performed to determine the PR8 virus-specific neutralizing titer of the sera as previously described (Sha et al. (1999) *Immunobiology* 200:21). 80–120 PFU of influenza A/PR8 virus was mixed with a sera at 50, 200, 1000 and 5000-fold dilutions and incubated at room temperature for 1 hour. Aliquots of 200 µl were added onto confluent MDCK cell monolayers in 6 well plates and incubated at 37° C. for 1 hour, and the plates were shaken gently every 15 minutes. After washing, 1.95% white agar in 1×DMEM medium containing 1 µg trypsin was overlaid on the wells. After incubation at 37° C. for 4 days, plates were stained with neutral red agar. The numbers of the plaques in each well were counted. The neutralizing antibody titer is the highest dilution of the serum that was found to reduce the number of the plaques by at least 50%.

Example 4

Antibody Responses

Influenza virus-specific antibodies were measured by enzyme-linked immunosorbent assay (ELISA) as previously described (Pertmer et al. (1996) *J. Virol.* 70:6119). Briefly, the assays were performed in 96-well plates (Dynatech, Alexandria, Va.) coated with purified PR8 virus at a concentration of 2 µg/ml in BBS buffer. Dilutions of serum were incubated overnight on coated and blocked ELISA plates, and the plates were then incubated with horseradish peroxidase-linked goat anti-mouse IgG (Southern Biotechnology Associates, Birmingham, Ala.). After washing with PBS plus 0.05% Tween 20, the substrate ABRS (2.2'-azino-bis-[3-ethylbenzthiazoline sulfonic acid]) (Sigma Chemical Co., St. Louis, Mo.) in phosphate citrate buffer (3 mg/10 ml) (pH 4.2) containing 0.03% $H_2O_2$ was added. After 30 minute incubation, the color was measured using an ELISA reader at 405 nm. Each sample was measured in duplicate. For determination of the relative levels of PR8-specific IgG subtype responses, a quantitative assay was performed. Standard curves were obtained by adding purified mouse IgG2a, IgG2a, IgG2b, and IgG3 to plates captured with a precoated goat anti-mouse Ig antibody, and colors were developed with ABTS substrate and HRP conjugated goat antibodies against each IgG subtype. Concentrations of the IgG1, IgG2a, IgG2b and IgG3 were determined by comparing the reading of the experimental samples with the standard curves.

Example 5

In vivo $CD8^+$ T Cell Depletion $CD8^+$ T cells were depleted in vivo by i.p. injection of purified rat anti-mouse CD8 monoclonal antibody (clone GK 1.5) (Wilde et al. (1983) *J. Immunol.* 131:2178). Antibodies were purified by a HiTrap Protein G colunm (Pharmacia Biotech, Uppsala, SE) from the supernatant of hybridoma GK1.5 cultures. 100 µg of antibody was injected i.p. to mice at days −3, −2, −1, and +1 of the immunization, and the injections were repeated every 5 days thereafter. The effectiveness of depletion was confirmed by FACS (Becton Dickinson Co., Mountain View, Calif.) analysis of staining of peripheral blood leukocytes of killed mice, and these samples were found to be 98–99% free of $CD8^+$ T cells.

Example 6

Flow Cytometry Analysis

Single cell suspensions from spleens of mice were made, and 1×106 cells were stained with anti-TCRβ, anti-CD8 and anti-CD4 monoclonal antibodies (H57-FITC, 53-6.7 PerCP and GK1.5-PE, respectively) (PharMingen, Becton-Dickinson, Inc.) for 30 minutes at 4° C. in 100 µl of FACS buffer (phosphate-buffered saline containing 0.3% bovine serum albumin and 0.1% sodium azide). Cells were washed with FACS buffer and fixed with 2% paraformalydehyde and then analyzed for single-, double- and three-color flow cytometry analysis on a FACScan (Becton Dickinson, Inc.). 10,000–20,000 events were counted for each sample. Forward and side scattered characteristics were used to distinguish the lymphocyte population. CELLQuest software (Becton Dickinson, Inc.) was used for the analysis.

Example 7

Challenge Studies

For procedures requiring a lethal challenge of influenza virus, a mouse-adapted, antigenically identical strain of A/PR/8/34 (a gift from Dr. Jiri Mestecky, Dept. of Microbiology, University of Alabama, Birmingham) was used for intranasal inoculation. 10×LD50 (500 PFU) of virus was administered by instillation into the nostrils of the anesthetized mice in a volume of 50 µl. Mice were observed daily, and all deaths were recorded.

REFERENCES

1. Bachmann et al. (1993) *J. Virol* 67:3917.
2. Bachmann et al. (1995) *Eur. J. Immunol.* 25:3445.
3. Davis et al. (1993) *Cell* 73:237
4. Evans et al. (1985) *Nature* 314:548.
5. Finkelman et al. (1990) *Annu. Rev. Immunol.* 8:303.
6. Freeret al. (1994) *J. Virol.* 68:3650.
7. Holaday et al. (1991) *J. Immunol.* 147:1653
8. Horstmann, D. M. (1979) *Rev. Infect. Dis.* 1:502.
9. Horstmann, D. M. (1982) *Dis.* 146:540.
10. Klenk et al. (1983) *Curr. Top. Microbio. Immunol.* 104:247
11. Locksley et al. (1993) *Science* 261:1448
12. Maloy et al. (1998) *Proc. Natl. Acad. Sci. USA* 95:1160.
13. Mitchell G. F. (1983) *J. Immunogenet.* 10:395
14. Mombaerts et al. (1992) published erratum appears in *Nature* Dec. 3, 1992 :360(6403):492. *Nature* 360:225
15. Mombaerts et al. (1994) *Int. Immunol.* 6:1061
16. Mond et al. (1995a) *Annu. Rev. Immunol.* 13:655.
17. Mond et al. (1995b) *Curr. Opin. Immunol.* 7:349.
18. Mosier et al. (1977) The ontogeny of thymic independent antibody responses in vitro in normal mice and mice with an X-linked B cell defect. *J. Immunol.* 119:1874.
19. Nkowane et al. (1987) *Jama* 257:1335.
20. Oxenius et al. (1998) *Adv. Immunol.* 70:313.

21. Parker, D. C. (1993) *Annu. Rev. Immunol* 11:331.
22. Pertmer et al. (1996) *J. Virol.* 70:6119
23. Rahemtulla, et al. (1991) *Nature* 353:180
24. Sabin et al. (1985) *J. Infect. Dis.* 151:420.
25. Salk, J., and Salk D. (1977) *Science* 195:834.
26. Sha et al. (199) *Immunobiology* 200:21
27. Snapper, C. M. and Mond, J. J. (1993) *Immunol. Today* 14:15.
28. Szomolanyi-Tsuda, E. and Welsh, R. M. (1996) *J. Exp. Med.* 183:403.
29. Szomolanyi-Tsuda et al. (1998) *J. Virol.* 72:6665.
30. Szomolanyi-Tsuda, E and Welsh, R. M. (1998) *Curr. Opin, Immunol.* 10:431
31. Viney et al. (1994) *Proc. Natl. Acad. Sci. USA* 91:11948
32. Wen (1996) *J. Exp. Med.* 183:2271
33. Weis et al. (1988) *Nature* 333:426
34. Wilde et al. (1983) *J. Immunol.* 131:2178

We claim:

1. A method for inducing an immune response against an influenza virus in a human or animal wherein said human or animal has a deficiency in CD4+ T cells, and said method comprising the step of administering to said human or animal an immunogenic composition comprising an inactivated intact influenza virus whereby a humoral immune response specific for the virus is induced.

2. The method of claim 1 wherein said virus is inactivated with formalin or beta-propiolactone.

* * * * *